United States Patent
Wang et al.

(10) Patent No.: US 11,919,876 B2
(45) Date of Patent: Mar. 5, 2024

(54) PROCESS AND SYSTEM TO MAKE OLEFIN EPOXIDES

(71) Applicant: ExxonMobil Technology and Engineering Company, Annandale, NJ (US)

(72) Inventors: Kun Wang, Branchburg, NJ (US); Timothy D. Shaffer, Plainfield, NJ (US)

(73) Assignee: EXXONMOBIL TECHNOLOGY AND ENGINEERING COMPANY, Annandale, NJ (US)

(*) Notice: Subject to any disclaimer, the term of this patent is extended or adjusted under 35 U.S.C. 154(b) by 9 days.

(21) Appl. No.: 17/597,888

(22) PCT Filed: Jun. 30, 2020

(86) PCT No.: PCT/US2020/040294
§ 371 (c)(1),
(2) Date: Jan. 28, 2022

(87) PCT Pub. No.: WO2021/021366
PCT Pub. Date: Feb. 4, 2021

(65) Prior Publication Data
US 2022/0169624 A1 Jun. 2, 2022

Related U.S. Application Data

(60) Provisional application No. 62/881,426, filed on Aug. 1, 2019.

(51) Int. Cl.
*C07D 301/19* (2006.01)
(52) U.S. Cl.
CPC .................................. *C07D 301/19* (2013.01)

(58) Field of Classification Search
CPC ........................... C07D 301/19; C07D 303/04
(Continued)

(56) References Cited

U.S. PATENT DOCUMENTS

| 3,887,361 A | 6/1975 | Lemke |
| 4,036,905 A | 7/1977 | Kornfeld |

(Continued)

FOREIGN PATENT DOCUMENTS

| CN | 103958488 A | 7/2014 |
| EP | 1621527 A1 | 2/2006 |

(Continued)

OTHER PUBLICATIONS

PCT/US2020/040294 International Search Report and Written Opinion dated Oct. 16, 2020.
(Continued)

*Primary Examiner* — Taylor V Oh
(74) *Attorney, Agent, or Firm* — Shook, Hardy & Bacon L.L.P.

(57) ABSTRACT

Processes and systems for producing olefin epoxides with three or more carbon atoms by oxidation of the corresponding branched hydrocarbons using oxygen are disclosed. An example process for producing olefin epoxides may include oxidizing a branched alkane to produce at least an organic hydroperoxide. The example process may further include epoxidizing a branched alkene by a catalytic reaction with least a portion of the organic hydroperoxide to produce at least an olefin epoxide and an alcohol. The example process may further include converting at least a portion of the alcohol to either additional branched alkane and/or additional branched alkene.

13 Claims, 2 Drawing Sheets

(58) Field of Classification Search
USPC .......................................................... 549/529
See application file for complete search history.

(56) References Cited

U.S. PATENT DOCUMENTS

| | | |
|---|---|---|
| 4,661,463 A | 4/1987 | Mocella |
| 9,637,423 B1 | 5/2017 | Wang et al. |
| 9,637,424 B1 | 5/2017 | Wang |
| 9,688,626 B2 | 6/2017 | Wang et al. |
| 10,011,777 B2 | 7/2018 | Roberts et al. |

FOREIGN PATENT DOCUMENTS

| | | |
|---|---|---|
| GB | 1111945 A | 5/1968 |
| WO | 2005090324 A1 | 9/2005 |
| WO | 2013057121 A1 | 4/2013 |
| WO | 2018203179 A1 | 11/2018 |

OTHER PUBLICATIONS

Matsuyama, et al., "Effects of trialkyl borates on Mo(VI)-catalyzed epoxidation of less reactive unsaturated compounds using t-butyl hydroperoxide", Studies of Surface Science and Catalysis, 145 (Science and Technology in Catalysis, 2002), 2003. 511-512.
Office Action received for China Application No. 202080052553.5, dated Oct. 23, 2023, 6 pages.
Kantam M. et al., "Molybdenum catalyzed dehydration of tertiary alcohols to olefins", Synthetic Communications, 1993, pp. 45-48. 23(1).

PROCESS AND SYSTEM TO MAKE OLEFIN EPOXIDES

CROSS-REFERENCE TO RELATED APPLICATIONS

This application is the 35 USC § 371 National Stage Application for PCT Application Number PCT/US2020/040294, filed on Jun. 30, 2020, which claims the benefit of U.S. Provisional Application No. 62/881,426, filed on Aug. 1, 2019, the entire contents of both of which are incorporated herein by reference.

FIELD

This application relates to processes and systems for producing olefin epoxides with three or more carbon atoms by oxidation of the corresponding branched hydrocarbons (alkanes or alkenes) using oxygen.

BACKGROUND

Olefin epoxides are an important intermediate that can be converted to many useful products, for example, olefin epoxides may be converted to surfactants, detergents, esters, and epoxies. In some instances, epoxides such as isobutylene epoxide can be converted to lactone (by carbonylation) and further to polylactone. Epoxides such as isobutylene epoxide can also be converted to polycarbonates by copolymerization with carbon dioxide. Olefin epoxides can be produced by oxidation of olefins with an epoxidation agent. During the epoxidation, an oxygen atom is transferred from the epoxidation agent to C=C double bond in the olefins, thus forming a three-membered ring with two carbon and one oxygen. Suitable epoxidation agents may typically include peracids, hydroperoxides, hydrogen peroxide, ozone, or $O_2$ (in the case of ethylene oxide).

All existing technologies require olefins as feeds, which can be produced by steam cracking, catalytic cracking, or catalytic dehydrogenation of alkanes. Since olefin generation from alkanes is a highly endothermic process, finding alternative, less energy-intensive processes to produce olefin epoxides from alkanes is desirable.

SUMMARY

Disclosed herein is an example process for producing olefin epoxides. The example process may include oxidizing a branched alkane to produce at least an organic hydroperoxide. The example process may further include epoxidizing a branched alkene by a catalytic reaction with least a portion of the organic hydroperoxide to produce at least an olefin epoxide and an alcohol. The example process may further include converting at least a portion of the alcohol to either additional branched alkane and/or additional branched alkene.

Further disclosed herein is another example process for producing olefin epoxides. The example process may include oxidizing a branched alkane stream comprising isobutane to produce at least t-butyl hydroperoxide. The example process may further include epoxidizing isobutylene by a catalytic reaction with at least a portion of the t-butyl hydroperoxide to produce at least isobutylene epoxide and t-butyl alcohol. The example process may further include dehydrating at least a portion of the t-butyl alcohol to produce water and additional isobutylene for the step of epoxidizing.

Further disclosed herein is an example system for producing olefin epoxides. The example system may include an oxidizer operable to receive a branched alkane stream and an oxygen stream and produce at least a hydroperoxide stream. The example system may further include an epoxidation reactor fluidically coupled to the oxidizer and operable to receive at least a portion of the hydroperoxide stream and a branched alkene stream and produce at least an alcohol stream and a product stream comprising an olefin epoxide. The example system may further include a reactor fluidically coupled to the epoxidation reactor operable to receive at least a portion of the alcohol stream.

BRIEF DESCRIPTION OF THE DRAWINGS

These drawings illustrate certain aspects of the present disclosure and should not be used to limit or define the disclosure.

DETAILED DESCRIPTION

Figure 1:
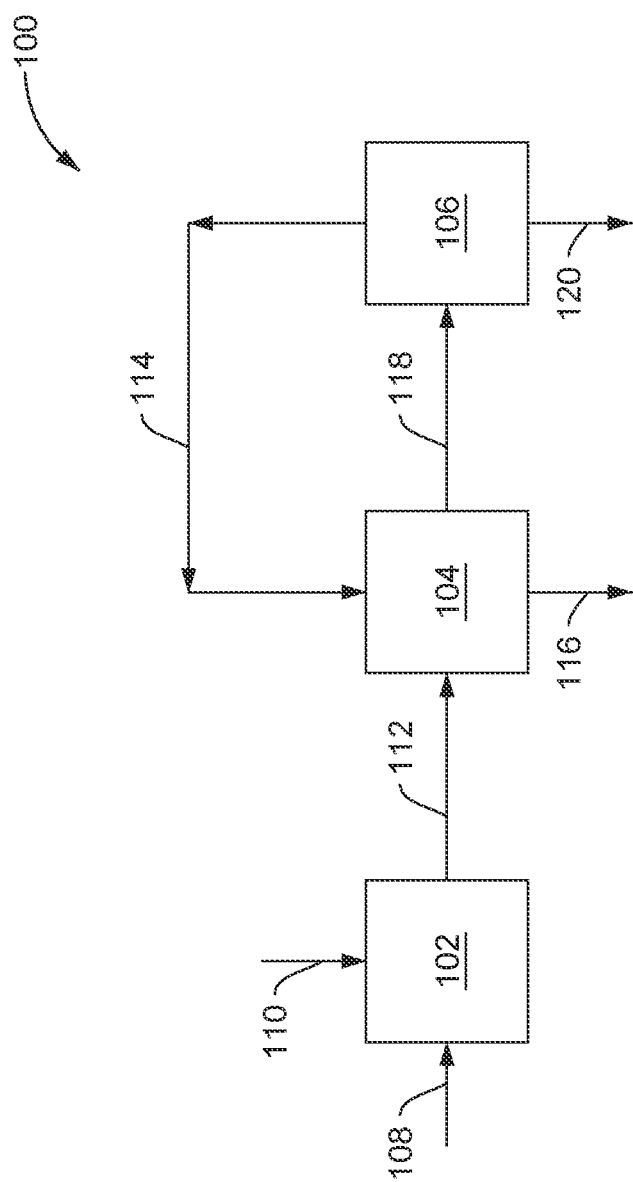
FIG. 1 is a schematic diagram of a process for production of olefin epoxides in accordance with embodiments of the present disclosure.

This application relates to processes and systems for producing olefin epoxides with three or more carbon atoms by oxidation of the corresponding hydrocarbons (alkanes and or alkenes) using oxygen or air.

There may be several potential advantages to the methods and systems disclosed herein, only some of which may be alluded to in the present disclosure. As discussed above, olefin epoxides can be an important intermediate in the production of many useful products. Advantageously, embodiments provide processes and systems that react alkanes with oxygen (air) for production of olefin oxides with three or more carbon atoms. The process and systems may be particularly advantageous as embodiments may produce olefin oxides in an integrated process that uses only branched hydrocarbons, oxygen, and optionally hydrogen. Suitable branched hydrocarbons may include can be an iso-paraffin or an iso-alkene. For example, an iso-alkane may be used with oxygen in an integrated process for the production of olefin epoxides. By way of further example, an iso-alkene may be used with oxygen and nitrogen in an integrated process for the production of olefin epoxides. In at least one embodiment, the organic hydroperoxide may be produced in the process from oxidation of an iso-paraffin. Accordingly, the methods and systems disclosed may enable efficient large-scale production of olefin oxides from readily available materials, such as iso-paraffins and iso-alkenes.

Embodiments may include an integrated process for the oxidation of hydrocarbons to produce olefin epoxides. The process may include the following steps: (1) oxidation of a branched alkane to an organic hydroperoxide; (2) epoxidizing a branched alkene using the organic hydroperoxide to produce an olefin epoxide and an alcohol corresponding to the branched alkane; and (3) converting the alcohol to produce a branched alkane or a branched alkene. The olefin epoxide produced in Step (2) may include three or more carbon atoms. The branched alkene produced in Step (3) may include, for example, the branched alkene from Step (2). By way of example, the alcohol conversion of Step (3) may include dehydration of the alcohol to produce the branched alkene. By way of further example, the alcohol conversion of Step (3) may include dehydration of the alcohol in the presence of hydrogen to produce the branched alkane.

In Step (1), any suitable technique for oxidation of branched alkanes to an organic hydroperoxide may be used. By way of example, the oxidation may include reaction of the branched alkanes and oxygen in the liquid phase. The oxidation may be autocatalytic with no catalyst required. However, in some embodiments, a small amount of initiator may be used. For example, the initiator may be used in an amount of about 50 parts per million ("ppm) to about 10000 ppm. Suitable initiators may include, but are not limited to, the hydroperoxide generated from the branched alkane, t-butyl hydroperoxide, cumyl hydroperoxide, 1-phenylethyl hydroperoxide, di-t-butyl peroxide, di-cumyl peroxide, azo-bisisobutyronitrile (AIBN), 1,1'-azobis(cyanocyclohexane) (ACHN). In at least one embodiment, the reaction may be carried out in a reaction medium that is devoid of any substantial amount of metals in an ionic state, for example, to provide a reaction medium in which the organic hydroperoxide is stable. In at least one embodiment, water may be added to the reaction mixture in excess of that present as a result of the oxidation process. By way of example, water may be added in an amount of at least 1 wt % water based on the weight of the reaction mixture, for example, from about 1 wt % water to about 6 wt % water by weight of the reaction mixture. By way of further example, the oxidation may be carried out in a dense phase reaction mixture, that is the oxidation may be carried out above the critical pressure of the mixture and under a specified temperature (e.g., about 140° C. to about 170° C.) so that the reaction mixture behaves as a single, dense, quasi-liquid phase. In the dense-phase embodiments, for example, the oxidation may be conducted in a series of corresponding reaction zones. By way of yet another example, the oxidation exothermic heat of reaction may be removed by circulating a portion of the reaction mixture through an indirect heat exchange with the oxygen introduced by sparging into the cooled, circulating reaction mixture. In at least one embodiment, the oxidation of Step (1) may include the co-production of an alcohol. In some embodiments, the oxidation may be optimized to maximize the selectivity to the organic hydroperoxide, although the alcohol co-product can be used in Step (3) for production of the branched hydrocarbon.

Any of a variety of branched alkanes may be used in the oxidation of Step (1). Suitable branched alkanes may have, for example, from 4 carbon atoms to 30 carbon atoms. Specific examples of suitable branched alkanes may include, but are not limited to, iso-butane, iso-pentane, iso-hexane, iso-heptane, and iso-octane, among others. In some embodiments, the branched alkanes may include cyclic branches, which may be aromatic or non-aromatic. An example of a suitable branched alkanes is provided below:

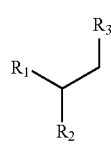

Structure 1

Wherein $R_1$ is a hydrocarbyl group having from 1 carbon atom to 10 carbon atoms, which may be linear, branched, or cyclic, $R_2$ is a hydrocarbyl group having from 1 carbon atom to 10 carbon atoms, which may be linear, branched, or cyclic, and $R_3$ is a hydrogen or a hydrocarbyl group having from 1 carbon atom to 9 carbon atoms, which may be linear, branched, or cyclic. Where cyclic, $R_1$, $R_2$, or $R_3$ may be aromatic or non-aromatic. In at least one embodiment, $R_1$ and $R_2$ are methyl groups while $R_3$ is hydrogen. In some embodiments, $R_1$ and $R_2$ may be connected as part of a 4- to 14-membered ring, as provided below:

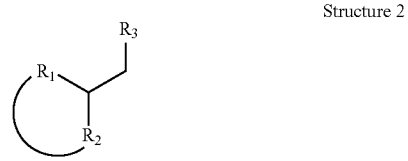

Structure 2

The 4- to 14-membered ring containing $R_1$ and $R_2$ may be saturated, single or multiple unsaturated, or aromatic.

Any suitable source of oxygen may be used in the oxidation of Step (1), for example, so that the oxygen-to-hydrocarbon vapor ratio may be maintained outside the explosive regime. For example, source of oxygen may include air (approximately 21 vol % oxygen), a mixture of nitrogen and oxygen, or pure oxygen. The mixture of nitrogen and oxygen may contain, for example, about 2 vol % to about 20 vol % oxygen.

The oxidation of Step (1) may have any suitable oxidation conditions, including temperature, pressure, and residence time. For example, the oxidation of step (1) may occur at a temperature of about 100° C. or greater. In some embodiments, the temperature of the oxidation may range from about 110° C. to about 200° C. or, alternatively, from about 130° C. to about 160° C. In some embodiments, the oxidation may be at a pressure of about 300 psig (2068 kpa) to about 800 psig (5526 kpa) or, alternatively, about 400 psig (2758 kpa) to about 600 psig (4199 kpa) or, alternatively, about 450 psig (3102 kpa) to about 550 psig (3792 kpa). In some embodiments, the residence time in the oxidation reactor (e.g., oxidation reactor 102 on FIG. 1 or 2) may be about 2 hours to about 24 hours, about 4 hours to about 10 hours, or about 6 hours to about 8 hours. The residence time may be selected to give a conversion to the organic hydroperoxide of about 15% to about 70%, about 20% to about 60%, or about 30% to about 50%. Where alcohol is co-product of the oxidation, the reaction conditions may be selected to provide a selectivity to the organic hydroperoxide of at least 50%, for example, of about 50% to about 80% with selectivity to the alcohol of about 20% to about 50%.

In Step (2), the epoxidation of the branched alkene using the organic hydroperoxide may be carried out using a catalyst. In some embodiments, a soluble catalyst may be used that includes a metal, such as Re, Mo, Nb, Ti, Ta, or mixtures thereof. An example of a suitable catalyst may have a Mo(VI)-oxo core such as molybdenum dioxide bis(acetylacetonate). Any suitable amount of the catalyst may be used for catalyzing the epoxidation, including, an amount of about 0.001 mol % to about 5 mol % of the total moles of reactants, about 0.01 mol % to about 4 mol %, or about 0.1 mol % to about 2 mol %. Basic promoters may be also be used in the epoxidation. Examples of suitable basic promoters may include, but are not limited to, amines, phosphines, phosphine oxides, or alkyl borate esters. Any suitable amount of the basic promoter may be used, including about 0.001 mol % to about 10 mol % of the total moles of reactants, about 0.01 mol % to about 8 mol %, or about 0.1 mol % to about 5 mol %. The epoxidation may be performed with or without a solvent. Where used, suitable solvents may include, but are not limited to, methanol, ethanol, isopropyl alcohol, and t-butyl alcohol. Other solvent such as ethers, hydrocarbons such as C10+ paraffins, cyclo-paraffins, aromatics such as toluene, xylenes, can also be used as long as it can provide the necessary solubility for the catalyst in the reaction mixture. However, t-butyl alcohol may be used, in some embodiments, as it may already be produced as the alcohol in Step (2) and/or a co-product of Step (1), potentially avoiding the need for any additional chemicals in the process.

Any of a variety of branched alkenes may be used in the epoxidation of Step (2). Suitable branched alkenes may have, for example, from 4 carbon atoms to 30 carbon atoms. Specific examples of suitable branched alkenes may include, but are not limited to, iso-butene, iso-pentenes, iso-hexenes, iso-heptenes, and iso-octenes, among others. In some embodiments, the branched alkenes may include cyclic branches, which may be aromatic or non-aromatic. Examples of a suitable branched alkenes may include, for example, 4 carbon atoms, 5 carbon atoms, 6 carbon atoms, or 7 carbon atoms. One example of a suitable branched alkenes may include isobutylene. In some embodiments, the branched alkenes may include cyclic branches, which may be aromatic or non-aromatic. An example of a suitable iso-alkene is provided below:

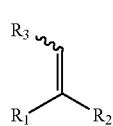

Structure 3

Wherein $R_1$ is a hydrocarbyl group having from 1 carbon atom to 10 carbon atoms, which may be linear, branched, or cyclic, $R_2$ is a hydrocarbyl group having from 1 carbon atom to 10 carbon atoms, which may be linear, branched, or cyclic, and $R_3$ is a hydrogen or a hydrocarbyl group having from 1 carbon atom to 9 carbon atoms, which may be linear, branched, or cyclic. Where cyclic, $R_1$, $R_2$, or $R_3$ may be aromatic or non-aromatic. In at least one embodiment, $R_1$ and $R_2$ are methyl groups while $R_3$ is hydrogen. In some embodiments, $R_1$ and $R_2$ may be connected as part of a 4- to 14-membered ring.

The epoxidation of Step (2) may be performed, for example, in a solution or a slurry at any suitable reaction conditions, including temperature, pressure, and residence time. For example, the epoxidation of step (2) may occur at a temperature of about 30° C. to about 200° C., about 130° C. to about 200° C., or about 75° C. to about 125° C. In some embodiments, the epoxidation may be at a pressure of about 15 psig (103 kpa) to about 1500 psig (10342 kpa), about 30 psig (207 kpa) to about 1000 psig (6895 kpa), or about 100 psig (689 kpa) to about 500 psig (3447 kpa). In some embodiments, the residence time in the epoxidation reactor (e.g., epoxidation reactor XX on FIG. XX) may be about 0.1 hours to about 24 hours, about 0.5 hours to about 12 hours, or about 1 hour to about 8 hours. The reaction conditions may be selected, for example, to give a conversion to the olefin epoxide of about 90% or greater and selectivity to the olefin epoxide of about 90% or greater.

In Step (3), the alcohol produced in Step (2) may be converted to a branched alkane or a branched alkene. For example, the alcohol may be dehydrated to produce the branched alkene of Step (2). The dehydration to produce the branched alkane may be carried out, for example, in a fixed bed or slurry dehydrater (e.g., dehydration reactor 106 on FIG. 1). An acid catalyst may be used, for example, to catalyze the dehydration. Suitable acid catalyst may include, but are not limited to, crosslinked polystyrene resins containing crosslinked sulfonic acid or carboxylic acid groups (e.g., Dowex™ resin or Amberlyst™ resin), sulfonated fluoropolymers (e.g., Nation™), liquid acids such sulfuric acid, sulfonic acid, or phosphoric acid (neat or solid-supported on silica, alumina, or clay), alumina, aluminosilicates, acidic clay, zeolites (natural or synthetic), silicoaluminophosphates (SAPO), acidic ionic liquids, or acids, such as aluminum chloride or boron trifluoride.

The dehydration of Step (3) may be performed, for example, in the vapor phase at any suitable reaction conditions, including temperature, pressure, and residence time. For example, the dehydration of step (3) may occur at a temperature of about 150° C. to about 450° C. or, alternatively, about 200° C. to about 350° C. In some embodiments, the dehydration be at a pressure of about 100 psig (689 kpa) to about 500 psig (3509 kpa), about 100 psig (689 kpa) to about 400 psig (2820 kpa), or about 150 psig (1034 kpa) to about 300 psig (2068 kpa). In some embodiments, the residence time in the dehydrater (e.g., dehydration reactor 106 on FIG. 1 or dehydration-hydrogenation reactor 201 on FIG. 2) may be about 1 second to 5 hours or, alternatively, about 5 seconds to 2 hours, or about 10 seconds to 1 hour. The reaction conditions may be selected, for example, to give a conversion of the alcohol to the branched alkenes of about 80% or greater, or 85% or higher, or 90% or higher.

In an alternative embodiment, Step (3) may include dehydration of the alcohol to provide a branched alkene, and the branched alkene may be hydrogenated in the same reactor using a hydrogenation catalyst and hydrogen to produce the branched alkane, for example, the branched alkane of Step (1). The dehydration-hydrogenation may be carried out, for example, in a fixed bed or slurry reactor (e.g., dehydration-hydrogenation reactor 201 on FIG. 2). A bi-functional catalyst containing an acid function for dehydration and a metal function for hydrogenation, physical mixtures of an acid catalyst and a hydrogenation catalyst, stacked or separated zones of the acid catalyst and the hydrogenation catalyst can be used. Suitable acid catalyst may include, but are not limited to, crosslinked polystyrene resins containing crosslinked sulfonic acid or carboxylic acid groups (e.g., Dowex™ resin or Amberlyst™ resin), sulfonated fluoropolymers (e.g., Nation™), liquid acids such sulfuric acid, sulfonic acid, or phosphoric acid (neat or solid-supported on silica, alumina, or clay), alumina, aluminosilicates, acidic clay, zeolites (natural or synthetic), silicoaluminophosphates (SAPO), acidic ionic liquids, or acids, such as aluminum chloride or boron trifluoride. Suitable hydrogenation catalyst may include late metals such as W, Mo, Fe, Co, Ni, Rh, Ru, Ir, Pt, Pd, Sn, Zn, Ga, either mono-metallic, or as binary or tertiary alloys, supported on oxides such as silica, alumina, titanic, zirconia, magnesia, zinc oxide, clays, aluminosilicates, zeolites. Suitable bifunctional catalyst may include late metals such W, Mo, Fe, Co, Ni, Rh, Ru, Ir, Pt, Pd, Sn, Zn, Ga, either mono-metallic or as binary or tertiary alloys, supported on an acidic support such as alumina, aluminosilicates, acidic clay, zeolites (natural or synthetic), silicoaluminophosphates (SAPO).

The dehydration-hydrogenation of Step (3) may be performed, for example, in the vapor phase at any suitable reaction conditions, including temperature, pressure, and residence time. For example, the dehydration-hydrogenation of step (3a) may occur at a temperature of about 150° C. to about 450° C. or, alternatively, about 200° C. to about 350° C. In some embodiments, the dehydration-hydrogenation be at a pressure of about 100 psig (689 kpa) to about 500 psig (3509 kpa), about 100 psig (621 kpa) to about 400 psig (2820 kpa), or about 150 psig (1034 kpa) to about 300 psig (2068 kpa). A hydrogen partial pressure of 50 psig (345 kpa) to about 450 psig (3105 kpa), about 90 psig (689 kpa) to about 380 psig (2622 kpa), or about 130 psig (897 kpa) to about 280 psig (1932 kpa) In some embodiments, the residence time in the dehydration-hydrogenation reactor (e.g., dehydration-hydrogenation reactor 201 on FIG. 2) may be about 1 second to 5 hours or, alternatively, about 5 seconds to 2 hours, or about 10 seconds to 1 hour. The reaction conditions may be selected, for example, to give a conversion of the alcohol to the branched alkanes of about _80_% or greater, or 85% or higher, or 90% or higher.

FIG. 1 is a schematic diagram of an embodiment of an integrated process 100 for producing olefin epoxides using branched alkanes and oxygen. As illustrated, integrated process 100 may include an oxidation reactor 102, an epoxidation reactor 104, and a dehydration reactor 106. Integrated process 100 may begin with oxidation of the branched paraffin to an organic hydroperoxide in oxidation reactor 102. The organic hydroperoxide from oxidation reactor 102 may be used in epoxidation reactor 104 for epoxidation of a branched alkene to produce an olefin epoxide and an alcohol. The alcohol produced in epoxidation reactor 104 may be dehydrated in the dehydration reactor 106 to produce a branched alkene and water. The branched alkene may be recycled to epoxidation reactor 104, as shown on FIG. 1.

Oxidation reactor 102 may take branched alkane stream 108 and oxygen-containing stream 110 and produce hydroperoxide stream 112. Branched alkane stream 108 may include branched alkanes such as iso-paraffins, and oxygen-containing stream 110 may include oxygen. Examples of suitable iso-paraffins and sources of oxygen are discussed above with respect to Step (1). While branched alkane stream 108 and oxygen-containing stream 110 are shown being fed separately into oxidation reactor 102, it should be understood that these streams may be combined and co-fed into oxidation reactor 102, as desired for a particular application. In oxidation reactor 102, the oxygen and branched alkane may react to produce at least the organic hydroperoxide, as described previously with respect to Step (1).

From oxidation reactor 102, at least a portion of hydroperoxide stream 112 may be transported to epoxidation reactor 104. For example, at least 10 vol %, 20 vol %, 40 vol %, 60 vol %, 80 vol %, or 100 vol % of hydroperoxide stream 112 from oxidation reactor 102 may be transported to epoxidation reactor 104. Epoxidation reactor 104 may take hydroperoxide stream 112 and recycle branched alkene stream 114 to generate product stream 116 and alcohol stream 118. In epoxidation reactor 104, the branched alkenes from recycle branch alkene stream 114 and organic hydroperoxides from hydroperoxide stream 112 may react to produce at olefin epoxide and alcohol, as described previously with respect to Step (2). Product stream 116 may include olefin epoxide produced in epoxidation reactor 104, and alcohol stream 118 may include alcohol produced in epoxidation reactor 104. While hydroperoxide stream 112 and recycle branched alkene stream 114 are shown being fed separately into epoxidation reactor 104, it should be understood that these streams may be combined and co-fed into epoxidation reactor 104, as desired for a particular application. Product stream 116 containing the olefin epoxide may be withdrawn from epoxidation reactor 104 and further processed, for example, as desired for a particular application.

From epoxidation reactor 104, at least a portion of alcohol stream 118 may be introduced into dehydration reactor 106. For example, at least 10 vol %, 20 vol %, 40 vol %, 60 vol %, 80 vol %, or 100 vol % of alcohol stream 118 from epoxidation reactor 104 may be transported to dehydration reactor 106. Dehydration reactor 106 may take alcohol stream 118 and produce recycle branched alkene stream 114 and water stream 120. In dehydration reactor, the alcohol in the alcohol stream 118 may be dehydrated to produce at least branched alkenes and water, as discussed above with respect to Step (3). Suitable branched alkenes that may be produced in dehydration reactor 106 are described above with respect to Step (3). Recycle branched alkene stream 114 may include the branched alkenes, and water stream 120 may include the water. At least a portion of the branched alkenes produced in dehydration reactor 106 may be recycled to epoxidation reactor 104 in recycle branched alkene stream 114, as shown on FIG. 1. For example, at least 10 vol %, 20 vol %, 40 vol %, 60 vol %, 80 vol %, or 100 vol % of the branched alkenes from dehydration reactor 106 may be transported to epoxidation reactor 104.

An example embodiment of the reaction sequence for Steps (1) to (3) that may be implemented in the integrated process of FIG. 1 is shown below in corresponding Equations (1) to (3):

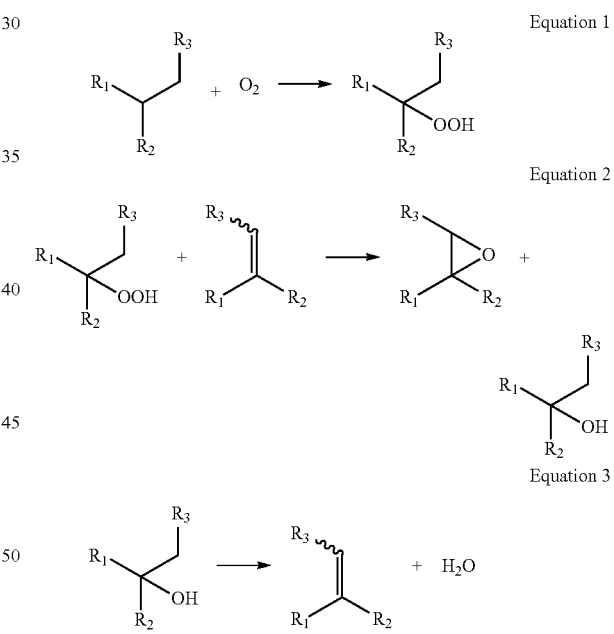

In embodiments of Equations (1) to (3), $R_1$ is a hydrocarbyl group having from 1 carbon atom to 10 carbon atoms, which may be linear, branched, or cyclic, $R_2$ is a hydrocarbyl group having from 1 carbon atom to 10 carbon atoms, which may be linear, branched, or cyclic, and $R_3$ is a hydrogen or a hydrocarbyl group having from 1 carbon atom to 9 carbon atoms, which may be linear, branched, or cyclic. Where cyclic, $R_1$, $R_2$, or $R_3$ may be aromatic or non-aromatic. In at least one embodiment, $R_1$ and $R_2$ are methyl groups while $R_3$ is hydrogen. In some embodiments, $R_1$ and $R_2$ may be connected as part of a 4- to 14-membered ring, as shown above in Structure (2) for an example branched paraffin of Step (1).

The net reaction for the embodiment of Equations (1) to (3) should be reaction of the branched paraffin with oxygen to yield the olefin epoxide and water, as shown below in Equation (4):

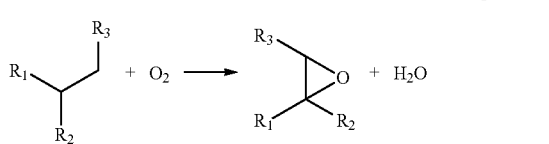
Equation 4

As previously discussed, the branched alkane used in the reaction scheme shown above in Equations (1) to (4), for example, may include a wide variety of hydrocarbons. In at least one embodiment, the branched alkane may include isobutane. By way of example, the process may include the following steps: (1) oxidation of isobutane to at least t-butyl hydroperoxide; (2) epoxidizing isobutylene using the t-butyl hydroperoxide to produce at least isobutylene epoxide and t-butyl alcohol; and (3) dehydrating the t-butyl alcohol to produce at least isobutylene. The isobutylene produced in Step (3) may be used in the epoxidation of Step (2). An example embodiment of the reaction sequence of Steps (1) to (3) for isobutane is shown below in Equations (5) to (6):

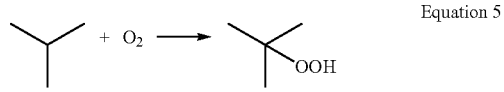
Equation 5

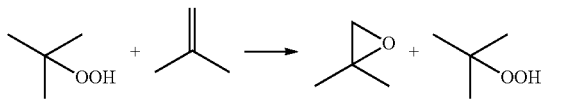
Equation 6

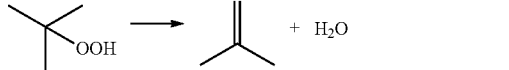
Equation 7

The net reaction for the embodiment of Equations (5) to (7) for isobutane should be reaction of isobutane with oxygen to yield isobutylene epoxide and water, as shown below in Equation (8):

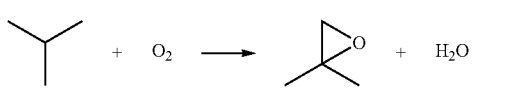
Equation 8

Figure 2:
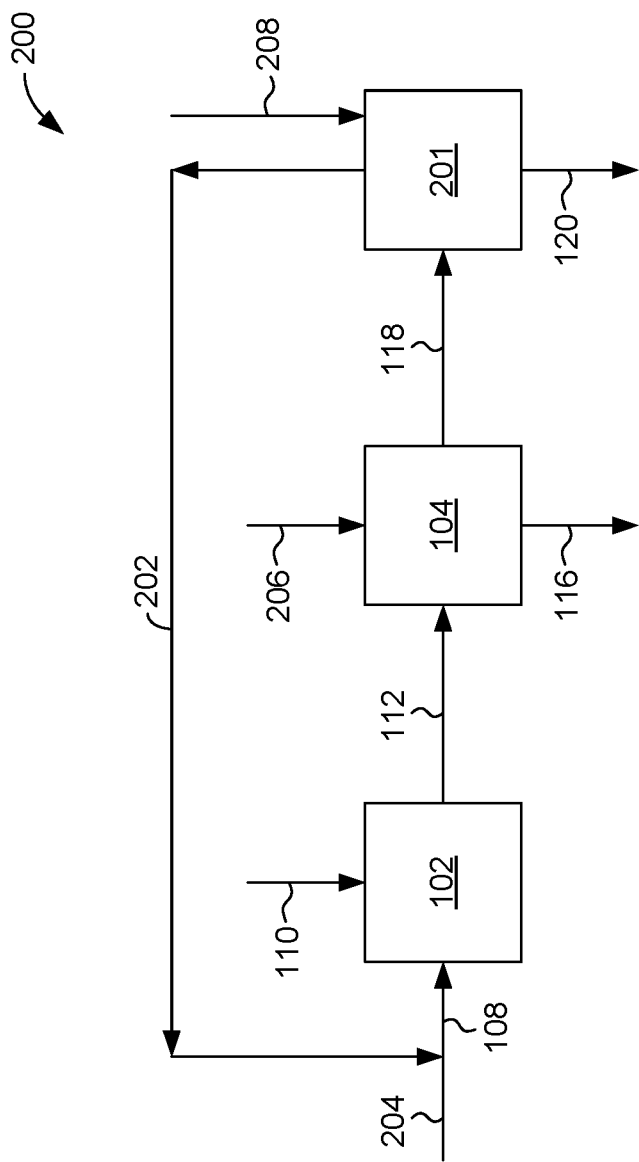
FIG. 2 is a schematic diagram of another process for production of olefin epoxides in accordance with embodiments of the present disclosure.

FIG. 2 is a schematic diagram of another embodiment of an integrated process 200 to produce olefin epoxides by oxidation of branched alkanes. As illustrated, the integrated process 200 may include an oxidation reactor 102, an epoxidation reactor 104, and a dehydration-hydrogenation reactor 201. Process 200 may begin with oxidation of the branched alkanes to an organic hydroperoxide in oxidation reactor 102. The organic hydroperoxide from oxidation reactor 102 may be used in epoxidation reactor 104 for epoxidation of a branched alkene to produce an olefin epoxide and an alcohol. The alcohol produced in epoxidation reactor 104 may be dehydrated and hydrogenated in the dehydration-hydrogenation reactor 201 to produce a branched alkane and water. The branched alkane may be recycled to oxidation reactor 102, as shown on FIG. 2.

Oxidation reactor 102 may take branched alkane stream 108 and oxygen-containing stream 110 and produce hydroperoxide stream 112. In oxidation reactor 102, the oxygen and branched alkane may react to produce at least the organic hydroperoxide, as described previously with respect to Step (1). Branched alkane stream 108 may include a branched alkane, and oxygen-containing stream 110 may include oxygen. Examples of suitable branched alkanes and sources of oxygen are discussed above with respect to Step (1). Branched alkane stream 108 may include recycle branched alkane stream 202 from dehydration-hydrogenation reactor 201, and make-up branched alkane stream 204. While recycle branched alkane stream 202 and make-up branched alkane stream 204 are shown being mixed prior to oxidation reactor 102, these streams (or portions thereof) may also be separately introduced to oxidation reactor 102. In addition, while branched alkane stream 108 and oxygen-containing stream 110 are shown being fed separately into oxidation reactor 102, it should be understood that these streams may be combined and co-fed into oxidation reactor 102, as desired for a particular application.

From oxidation reactor 102, at least a portion of hydroperoxide stream 112 may be transported to epoxidation reactor 104. For example, at least 10 vol %, 20 vol %, 40 vol %, 60 vol %, 80 vol %, or 100 vol % of hydroperoxide stream 112 from oxidation reactor 102 may be transported to epoxidation reactor 104. Epoxidation reactor 104 may take hydroperoxide stream 112 and branched alkene stream 206 to generate product stream 116 and alcohol stream 118. Branched alkene stream 206 may include iso-alkenes, for example, described above with respect to Step (2). In epoxidation reactor 104, the branched alkenes from branched alkene stream 206 and organic hydroperoxides from hydroperoxide stream 112 may react to produce at olefin epoxide and alcohol, as described previously with respect to Step (2). Product stream 116 may include olefin epoxide produced in epoxidation reactor 104, and alcohol stream 118 may include alcohol produced in epoxidation reactor 104. While hydroperoxide stream 112 and branched alkene stream 206 are shown being fed separately into epoxidation reactor 104, these streams may be alternatively combined and co-fed into epoxidation reactor 104, as desired for a particular application. Product stream 116 containing the olefin epoxide may be withdrawn from epoxidation reactor 104 and further processed, for example, as desired for a particular application.

From epoxidation reactor 104, at least a portion of alcohol stream 118 may be introduced into dehydration-hydrogenation reactor 201. For example, at least 10 vol %, 20 vol %, 40 vol %, 60 vol %, 80 vol %, or 100 vol % of alcohol stream 118 from epoxidation reactor 104 may be transported to dehydration-hydrogenation reactor 201. Dehydration-hydrogenation reactor 201 may take alcohol stream 118 and hydrogen to produce recycle branched alkane stream 202 and water stream 120. As illustrated, the hydrogen may be fed to dehydration-hydrogenation reactor 201 by a hydrogen stream 208. In the dehydration-hydrogenation reactor 201, the alcohol in alcohol stream 118 may be dehydrated to produce at least branched alkene and water. The branched alkenes are hydrogenated in the same reactor to produce recycle branched alkane stream 202, as discussed above with respect to Step (3). Recycle branched alkane stream 202 may include the iso-alkanes, and water stream 120 may include the water. At least a portion of the branched alkanes produced in dehydration-hydrogenation reactor 201 may be recycled to oxidation reactor 102 in recycle branched alkane stream 202, as shown on FIG. 2. For example, at least 10 vol %, 20 vol %, 40 vol %, 60 vol %, 80 vol %, or 100 vol % of the iso-alkanes from dehydration reactor 106 may be transported to oxidizer.

An example embodiment of the reaction sequence for Steps (1) to (3) that may be implemented in the integrated process of FIG. 2 is shown below in corresponding Equations (9) to (11):

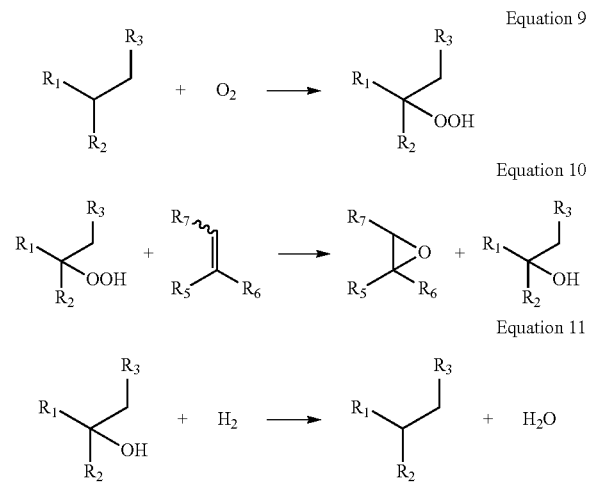

In embodiments of Equations (9) to (11), $R_1$ is a hydrocarbyl group having from 1 carbon atom to 10 carbon atoms, which may be linear, branched, or cyclic, $R_2$ is a hydrocarbyl group having from 1 carbon atom to 10 carbon atoms, which may be linear, branched, or cyclic, and $R_3$ is a hydrogen or a hydrocarbyl group having from 1 carbon atom to 9 carbon atoms, which may be linear, branched, or cyclic. Where cyclic, $R_1$, $R_2$, or $R_3$ may be aromatic or non-aromatic. In at least one embodiment, $R_1$ and $R_2$ are methyl groups while $R_3$ is hydrogen. In some embodiments, $R_1$ and $R_2$ may be connected as part of a 4- to 14-membered ring, as shown above in Structure (2) for an example branched alkane of Step (1).

In embodiments of Equations (9) to (11), $R_5$ is a hydrocarbyl group having from 1 carbon atom to 10 carbon atoms, which may be linear, branched, or cyclic, $R_6$ is a hydrocarbyl group having from 1 carbon atom to 10 carbon atoms, which may be linear, branched, or cyclic, and $R_7$ is a hydrogen or a hydrocarbyl group having from 1 carbon atom to 9 carbon atoms, which may be linear, branched, or cyclic. Where cyclic, $R_5$, $R_6$, or $R_7$ may be aromatic or non-aromatic. In some embodiments, $R_5$ and $R_6$ may be connected as part of a 4- to 14-membered ring, as shown below in Structure (4):

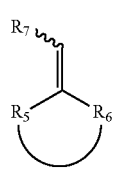

Structure 4

The ring structure shown on Structure 4 can be saturated or have varying degrees of unsaturation without constituting aromaticity.

The net reaction for the embodiment of Equations (9) to (11) should be reaction of the branched alkene with hydrogen and oxygen to yield the olefin epoxide and water, as shown below in Equation (12):

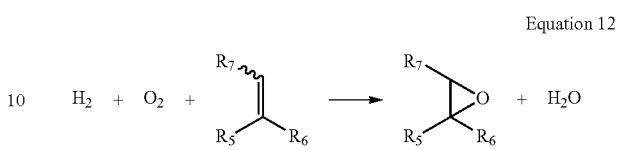

Equation 12

Accordingly, the preceding description describes examples of processes and systems for producing olefin epoxides with three or more carbon atoms from oxidation of corresponding branched hydrocarbons (alkanes or alkenes) using oxygen. The processes and systems disclosed herein may include any of the various features disclosed herein, including one or more of the following embodiments.

Embodiment 1. A process for producing olefin epoxides, comprising: oxidizing a branched alkane to produce at least an organic hydroperoxide; epoxidizing a branched alkene by a catalytic reaction with least a portion of the organic hydroperoxide to produce at least an olefin epoxide and an alcohol; and converting at least a portion of the alcohol to either additional branched alkane and/or additional branched alkene.

Embodiment 2. The process of embodiment 1, wherein the branched alkane has the following structure:

Structure 1 wherein $R_1$ is a hydrocarbyl group having from 1 carbon atom to 10 carbon atoms and is linear, branched, or cyclic, $R_2$ is a hydrocarbyl group having from 1 carbon atom to 10 carbon atoms and is linear, branched, or cyclic, and $R_3$ is a hydrogen or a hydrocarbyl group having from 1 carbon atom to 9 carbon atoms and is linear, branched, or cyclic.

Embodiment 3. The process of embodiment 2, wherein $R_1$ and $R_2$ are connected as part of a 4- to 14-membered ring.

Embodiment 4. The process of any preceding embodiment, wherein the branched alkane comprising isobutane, and wherein the olefin oxide comprises isobutylene epoxide.

Embodiment 5. The process of any preceding embodiment, wherein the step of oxidizing further produces additional alcohol.

Embodiment 6. The process of any preceding embodiment, wherein the step of oxidizing comprises reacting the branched alkane with oxygen, wherein a source of the oxygen is air.

Embodiment 7. The process of any preceding embodiment, wherein the step of epoxidizing is carried out using a soluble catalyst.

Embodiment 8. The process of embodiment 7, wherein the soluble catalyst comprises a molybdenum dioxide bis (acetylacetonate).

Embodiment 9. The process of any preceding embodiment, wherein the step of converting comprises dehydrating at least a portion of the alcohol to produce at least water and the additional branched alkene, and wherein the branched alkene from the step of epoxidizing comprises a quantity of the additional branched alkene that is produced in the step of converting.

Embodiment 10. The process of embodiment 1, wherein the step of converting comprises dehydrating and dehydrogenating at least a portion of the alcohol in the presence of hydrogen and a bifunctional catalyst to produce at least water and the additional branched alkane, wherein the branched alkane from the step of oxidizing comprises a quantity of the additional branched alkane produced in the converting, and wherein the bifunctional catalyst comprises a hydrogenation function and a dehydration function.

Embodiment 11. The process of embodiment 1:

wherein the step of oxidizing is represented by the following equation:

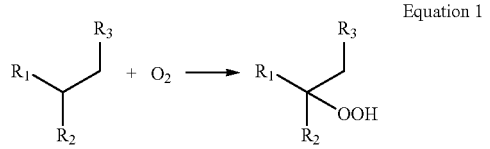

Equation 1 wherein the step of epoxidizing is represented by the following equation:

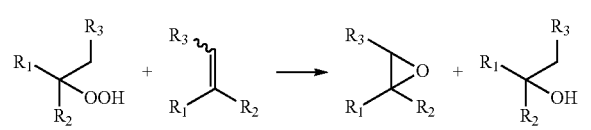

Equation 2 wherein the step of converting is represented by the following equation:

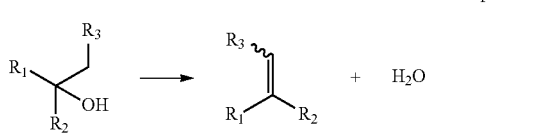

Equation 3 wherein $R_1$ is a hydrocarbyl group having from 1 carbon atom to 10 carbon atoms and that is linear, branched, or cyclic, $R_2$ is a hydrocarbyl group having from 1 carbon atom to 10 carbon atoms and that is linear, branched, or cyclic, and $R_3$ is a hydrogen or a hydrocarbyl group having from 1 carbon atom to 9 carbon atoms and that is linear, branched, or cyclic.

Embodiment 12. The process of embodiment 11, wherein $R_1$ and $R_2$ are methyl groups and $R_3$ is the hydrogen.

Embodiment 13. The process of any one of embodiments 1 to 9:

wherein the step of oxidizing is represented by the following equation:

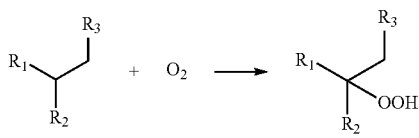

Equation 9 wherein the step of epoxidizing is represented by the following equation:

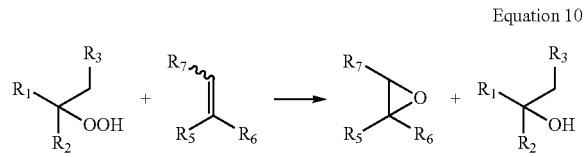

Equation 10 wherein the step of converting is represented by the following equation:

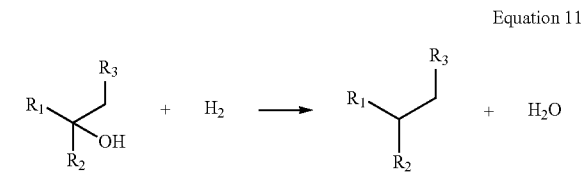

Equation 11 wherein $R_1$ is a hydrocarbyl group having from 1 carbon atom to 10 carbon atoms and that is linear, branched, or cyclic, $R_2$ is a hydrocarbyl group having from 1 carbon atom to 10 carbon atoms and that is linear, branched, or cyclic, and $R_3$ is a hydrogen or a hydrocarbyl group having from 1 carbon atom to 9 carbon atoms and that is linear, branched, or cyclic; and wherein $R_5$ is a hydrocarbyl group having from 1 carbon atom to 10 carbon atoms and that is linear, branched, or cyclic, $R_6$ is a hydrocarbyl group having from 1 carbon atom to 10 carbon atoms and that is linear, branched, or cyclic, and $R_7$ is a hydrogen or a hydrocarbyl group having from 1 carbon atom to 9 carbon atoms and that is linear, branched, or cyclic.

Embodiment 14. The process of embodiment 13 13, where $R_5$ and $R_6$ are connected as part of a 4- to 14-membered ring.

Embodiment 15. A process for producing olefin epoxides, comprising: oxidizing a branched alkane stream comprising isobutane to produce at least t-butyl hydroperoxide;

epoxidizing isobutylene by a catalytic reaction with at least a portion of the t-butyl hydroperoxide to produce at least isobutylene epoxide and t-butyl alcohol; and dehydrating at least a portion of the t-butyl alcohol to produce water and additional isobutylene for the step of epoxidizing.

Embodiment 16. The process of embodiment 15, wherein the oxidizing further produces additional t-butyl alcohol.

Embodiment 17. The process of embodiment 16, further comprising dehydrating at least a portion of the additional t-butyl alcohol.

Embodiment 18. The process of any one of embodiments 15 to 17, wherein the isobutylene in step of epoxidizing comprises a quantity of the isobutylene that is recycled from the step of dehydrating.

Embodiment 19. A system for producing olefin epoxides, comprising: an oxidizer operable to receive a branched alkane stream and an oxygen stream and produce at least a hydroperoxide stream; an epoxidation reactor fluidically coupled to the oxidizer and operable to receive at least a portion of the hydroperoxide stream and a branched alkene stream and produce at least an alcohol stream and a product stream comprising an olefin epoxide; and a reactor fluidically coupled to the epoxidation reactor operable to receive at least a portion of the alcohol stream.

Embodiment 20. The system of embodiment 19, wherein the reactor is fluidically coupled to the epoxidation reactor by a recycle branched alkene stream, and wherein the reactor comprises a bifunctional catalyst comprising a hydrogenation function and a dehydration function.

While the disclosure has been described with respect to a number of embodiments and examples, those skilled in the art, having benefit of this disclosure, will appreciate that other embodiments can be devised which do not depart from the scope and spirit of the disclosure as disclosed herein. Although individual embodiments are discussed, the present disclosure covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the disclosure, additionally, they do not exclude impurities and variances normally associated with the elements and materials used.

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

The invention claimed is:

1. A process for producing olefin epoxides, comprising:
oxidizing a branched alkane to produce at least an organic hydroperoxide;
epoxidizing a branched alkene by a catalytic reaction with least a portion of the organic hydroperoxide to produce at least an olefin epoxide and an alcohol; and
converting at least a portion of the alcohol to additional branched alkane and additional branched alkene,
wherein the step of converting comprises dehydrating at least a portion of the alcohol to produce at least water and the additional branched alkene, and wherein the branched alkene from the step of epoxidizing comprises a quantity of the additional branched alkene that is produced in the step of converting, and
wherein the step of converting comprises dehydrating and hydrogenating at least a portion of the alcohol in the presence of hydrogen and a bifunctional catalyst to produce at least water and the additional branched alkane, wherein the branched alkane from the step of oxidizing comprises a quantity of the additional branched alkane produced in the converting, and wherein the bifunctional catalyst comprises a hydrogenation function and a dehydration function.

2. The process of claim 1, wherein the branched alkane has the following structure:

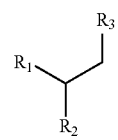

wherein $R_1$ is a hydrocarbyl group having from 1 carbon atom to 10 carbon atoms and is linear, branched, or cyclic, $R_2$ is a hydrocarbyl group having from 1 carbon atom to 10 carbon atoms and is linear, branched, or cyclic, and $R_3$ is a hydrogen or a hydrocarbyl group having from 1 carbon atom to 9 carbon atoms and is linear, branched, or cyclic.

3. The process of claim 2, wherein $R_1$ and $R_2$ are connected as part of a 4- to 14-membered ring.

4. The process of claim 1, wherein the branched alkane comprises isobutane, and wherein the olefin oxide comprises isobutylene epoxide.

5. The process of claim 1, wherein the step of oxidizing further produces additional alcohol.

6. The process of claim 1, wherein the step of oxidizing comprises reacting the branched alkane with oxygen, wherein a source of the oxygen is air.

7. The process of claim 1, wherein the step of epoxidizing is carried out using a soluble catalyst.

8. The process of claim 7, wherein the soluble catalyst comprises a molybdenum dioxide bis(acetylacetonate).

9. The process of claim 1:
wherein the step of oxidizing is represented by the following equation:

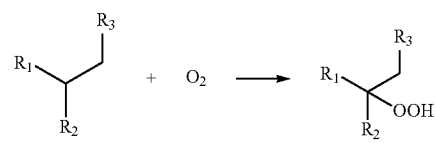

wherein the step of epoxidizing is represented by the following equation:

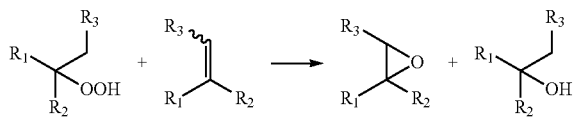

wherein the step of converting is represented by the following equation:

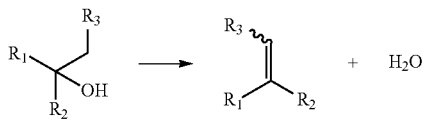

wherein $R_1$ is a hydrocarbyl group having from 1 carbon atom to 10 carbon atoms and that is linear, branched, or cyclic, $R_2$ is a hydrocarbyl group having from 1 carbon atom to 10 carbon atoms and that is linear, branched, or cyclic, and $R_3$ is a hydrogen or a hydrocarbyl group having from 1 carbon atom to 9 carbon atoms and that is linear, branched, or cyclic.

10. The process of claim 9, wherein $R_1$ and $R_2$ are methyl groups and $R_3$ is the hydrogen.

11. The process of claim 1:

wherein the step of oxidizing is represented by the following equation:

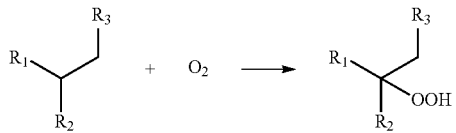

wherein the step of epoxidizing is represented by the following equation:

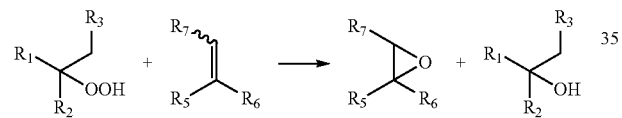

wherein the step of converting is represented by the following equation:

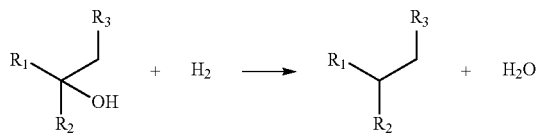

wherein $R_1$ is a hydrocarbyl group having from 1 carbon atom to 10 carbon atoms and that is linear, branched, or cyclic, $R_2$ is a hydrocarbyl group having from 1 carbon atom to 10 carbon atoms and that is linear, branched, or cyclic, and $R_3$ is a hydrogen or a hydrocarbyl group having from 1 carbon atom to 9 carbon atoms and that is linear, branched, or cyclic; and wherein $R_5$ is a hydrocarbyl group having from 1 carbon atom to 10 carbon atoms and that is linear, branched, or cyclic, $R_6$ is a hydrocarbyl group having from 1 carbon atom to 10 carbon atoms and that is linear, branched, or cyclic, and $R_7$ is a hydrogen or a hydrocarbyl group having from 1 carbon atom to 9 carbon atoms and that is linear, branched, or cyclic.

12. The process of claim 11, where $R_5$ and $R_6$ are connected as part of a 4- to 14-membered ring.

13. A process for producing olefin epoxides, comprising:

oxidizing a branched alkane stream comprising isobutane to produce at least t-butyl hydroperoxide;

epoxidizing isobutylene by a catalytic reaction with at least a portion of the t-butyl hydroperoxide to produce at least isobutylene epoxide and t-butyl alcohol;

dehydrating at least a portion of the t-butyl alcohol to produce water and additional isobutylene for the step of epoxidizing; and dehydrating and hydrogenating at least a portion of the t-butyl alcohol in the presence of hydrogen and a bifunctional catalyst to produce at least water and additional branched alkane, wherein the branched alkane from the step of oxidizing comprises a quantity of the additional branched alkane produced in the converting, and wherein the bifunctional catalyst comprises a hydrogenation function and a dehydration function.

\* \* \* \* \*